United States Patent
Kfir

(10) Patent No.: US 8,333,589 B2
(45) Date of Patent: Dec. 18, 2012

(54) ASSEMBLY FOR LIFTING THE SINUS MEMBRANE FOR USE IN DENTAL IMPLANT SURGERY

(75) Inventor: Efraim Kfir, Petach Tikva (IL)

(73) Assignee: Miambe Ltd. (IL)

( * ) Notice: Subject to any disclaimer, the term of this patent is extended or adjusted under 35 U.S.C. 154(b) by 812 days.

(21) Appl. No.: 12/300,005

(22) PCT Filed: May 3, 2007

(86) PCT No.: PCT/IL2007/000543
§ 371 (c)(1),
(2), (4) Date: Jan. 15, 2009

(87) PCT Pub. No.: WO2007/129312
PCT Pub. Date: Nov. 15, 2007

(65) Prior Publication Data
US 2009/0181345 A1    Jul. 16, 2009

(30) Foreign Application Priority Data

May 8, 2006 (IL) .......................................... 175477

(51) Int. Cl.
*A61C 8/00* (2006.01)

(52) U.S. Cl. .................................................... 433/173

(58) Field of Classification Search .......... 433/172–176; 604/500, 102.01, 99.01, 101.02, 101.04, 604/103.05, 103.07, 912
See application file for complete search history.

(56) References Cited

U.S. PATENT DOCUMENTS

| | | | |
|---|---|---|---|
| 5,318,529 A | 6/1994 | Kontos | 604/96 |
| 5,685,716 A | 11/1997 | Linkow | |
| 2006/0064071 A1* | 3/2006 | Bonnette et al. | 604/500 |
| 2006/0084034 A1 | 4/2006 | Hochman | 433/173 |
| 2009/0326484 A1* | 12/2009 | Levine et al. | 604/265 |
| 2010/0009314 A1* | 1/2010 | Tardieu et al. | 433/144 |
| 2010/0221681 A1* | 9/2010 | Hochman | 433/173 |

FOREIGN PATENT DOCUMENTS

| | | |
|---|---|---|
| DE | 43 21 785 | 3/1995 |
| DE | 100 36 027 | 1/2002 |

(Continued)

OTHER PUBLICATIONS

Notification Concerning Transmittal of International Preliminary Report on Patentability and the International Preliminary Report on Patentability dated Nov. 11, 2008 and the Written Opinion of the International Searching Authority (7 pages, total) for International Application PCT/IL2007/000543 with International Filing date May 3, 2007.

(Continued)

Primary Examiner — Sunil K Singh
(74) Attorney, Agent, or Firm — Ostrolenk Faber LLP

(57) ABSTRACT

An assembly for practicing sinus membrane elevation in the process of dental implant surgery comprising a balloon made of an elastomeric material and having a rounded head portion, an elongated, tubular sleeve portion and a flanged rim portion. Further provided is a balloon probe member having a stem portion with an outer screw-thread and a bore freely fitting the external diameter of the balloon tubular sleeve. A connector member is threadably receivable in the probe member and connected to a flexible pipe with a manually operable valve. For inflating the balloon a pump supplies a pressurized fluid through the pipe.

9 Claims, 7 Drawing Sheets

FOREIGN PATENT DOCUMENTS

| | | |
|---|---|---|
| EP | 1 174 094 A | 1/2002 |
| EP | 1 159 984 B1 | 7/2004 |
| JP | 5-237192 | 9/1993 |
| JP | 2006-192040 | 7/2006 |
| WO | WO 01/85062 | 11/2001 |

OTHER PUBLICATIONS

International Search Report dated Sep. 5, 2007, issued in corresponding international application No. PCT/IL2007/000543.

Japanese Office Action (Notice of Reason for Refusal) dated May 30, 2012.

E. Kfir et al., "Minimally Invasice Antral Membrane Balloon Elevation Followed by Maxillary Bone Augmentation and Implant Fixation", *Journal of Oral Implantology*, XXXII(1):26-33 (2006).

Office Action dated Jan. 31, 2012 issued in corresponding Japanese Patent Application No. 2009-508662 with English Translation (Total 3 pages).

\* cited by examiner

ASSEMBLY FOR LIFTING THE SINUS MEMBRANE FOR USE IN DENTAL IMPLANT SURGERY

CROSS REFERENCE TO RELATED APPLICATIONS

The present application is a 35 U.S.C. §371 National Phase conversion of PCT/IL2007/000543, filed May 3, 2007, which claims benefit of Israeli Application No. 175477, filed May 8, 2007, the disclosure of which is incorporated herein by reference. The PCT International Application was published in the English language.

BACKGROUND OF THE INVENTION

In the journal of Oral Implantology, Vol. XXXII No. 1 (2006) of February 2006, there has been published an article titled "Minimally by Invasive Antral Membrane Balloon Elevation Followed by Maxillary Bone Augmentation and Implant Fixation" (Dr. Efraim Kfir et al.) In the article there has been described implementation of a technique using a balloon for separating and lifting the Shneiderian membrane in order to gain more bone substrate for placement of maxillary dental implants.

This method has already been proposed in European Patent Application No. 1174094 published Jan. 23, 2002.

The general object of the present invention is to provide an apparatus for practicing this method in a safe and reliable manner.

It is a further object of the invention to provide a kit of parts that can be used repeatedly after autoclave sterilizations.

It is a still further object of the invention to ensure protection of the balloon within a dedicated probe during the insertion phase.

It is a still further object of the invention to provide means enabling exact extent of penetration of the balloon probe to avoid accidental rupture of the sinus membrane.

It is a still further object of the invention to reach sinus floor spreading-apart of over $10_{mm}$ in all directions.

SUMMARY OF THE INVENTION

According to the invention is provided an assembly for practicing sinus membrane elevation in the process of dental implant surgery comprising a balloon made of an elastomeric material comprising a rounded head portion, an elongated, tubular sleeve portion and a flanged rim portion; a balloon probe member having a stem portion with an outer screw-thread and a bore freely fitting the external diameter of the tubular sleeve, a shoulder configured to support the said balloon flanged rim portion, and cup-shaped portion with an inner screw thread therealong; a connector member threadably receivable in said cup-shaped portion at one side and configured to be coupled to a flexible pipe at the other side thereof; a flexible pipe with a manually operable valve; and a pump for administrating a pressurized fluid through the pipe to the balloon.

BRIEF DESCRIPTION OF THE DRAWINGS

These and additional constructional features and advantages of the invention will be more readily understood in the light of the ensuing description of a preferred embodiment thereof, given by way of example only, with reference to the accompanying drawings wherein:—

DETAILED DESCRIPTION OF THE PREFERRED EMBODIMENT

Figure 1:
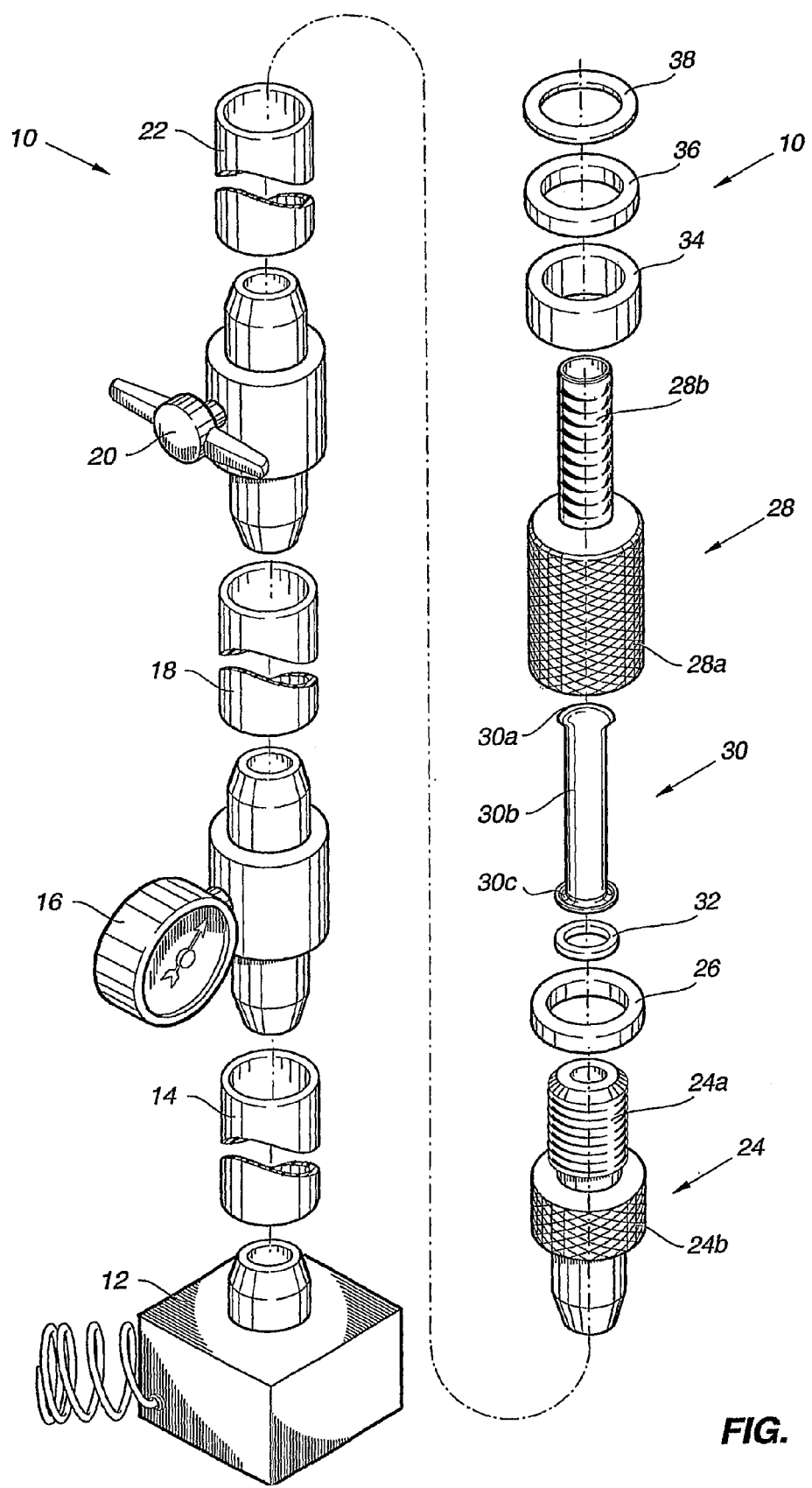
FIG. 1 is an exploded view of the assembly according to a preferred embodiment of the present invention.

Starting from bottom to the top of the assembly generally denoted 10 in FIG. 1, there is provided a pump 12 for delivering (and discharging) a fluid. The pump 12 may be electric or manual. The fluid may be a saline liquid.

From the pump there extends a first stretch of flexible transparent hose 14 leading to a pressure-gauge fitting 16. A second length of hose 18 is connected to valve 20 shown in the closed position.

A further pipe stretch 22 leads to a connector member designated 24. The connector 24 comprises an outer screw-threaded portion 24a and a preferably knurled ring-shaped shoulder 24b. The connector member 24 is connectable, after interposing seal ring 26, to balloon probe 28 which comprises a cup-shaped portion 28a and a tubular stem portion 28b. The portion 28a comprises an inner screw-threaded side wall 25 and an inner base wall, constituting an inner shoulder 27. Preferably, the portion 28a further has a knurled outer surface. The tubular stem portion 28b is of an inner diameter slightly greater than the outer diameter of balloon 30. The portion 28b has an osteotomy screw-thread.

The inner shoulder 27 is configured to support a balloon flanged rim 30c, as described below, when the balloon probe 28 is connected to the connector 24, i.e. when the screw-threaded portion 24a of the connector 24 is threadably received in the cup-shaped portion 28a of the probe 28.

Now, according to a major aspect of the invention, and unlike normal balloons made of thin and flappy sheet of Latex or the like rubber based materials, the balloon 30 is preferably made of Silicon rubber and in the form of a self-supporting article, having a rounded, mushroom-like, top 30a, merging into an elongated sleeve 30b provided with a flanged rim 30c. The balloon is preferably produced by a process known as "press-cure transfer and dipping" process in order to yield the following specifications:

- the mushroom head 30a should be of low modulus of elasticity (hardness of 16-40 shor) and high elongation factor (600%-1,300%);
- the remaining portions 30b and 30c are thicker and of high modulus (50-80 shor) and low elongation factor (250%-600%);
- the wall thickness of the balloon head 30a is about $0.2_{mm}$;
- the wall thickness of the sleeve portion 30b is about $0.3_{mm}$;

Thus, the balloon 30 is self-contained, adapted to be conveniently gripped by a tongs or even by hand whenever requested, e.g. carried to or from an autoclave for sterilization between repeated uses. No strips, ties, or glue are involved as will be appreciated from the description given further below.

Figure 2C:
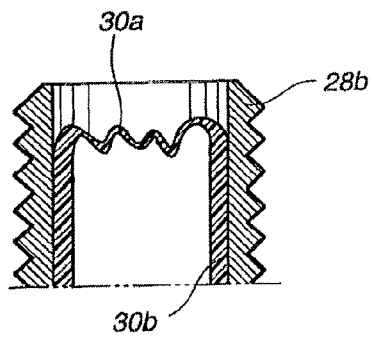
FIG. 2c is a detail of FIG. 2a illustrating in cross-section view a portion of the tubular stem portion.
Figure 2B:
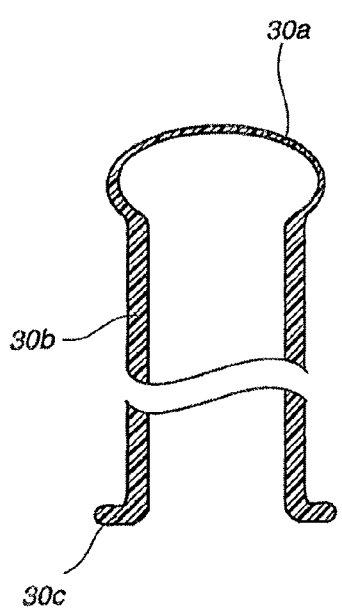
FIG. 2b is a detail of FIG. 2a on an enlarged scale.
Figure 2A:
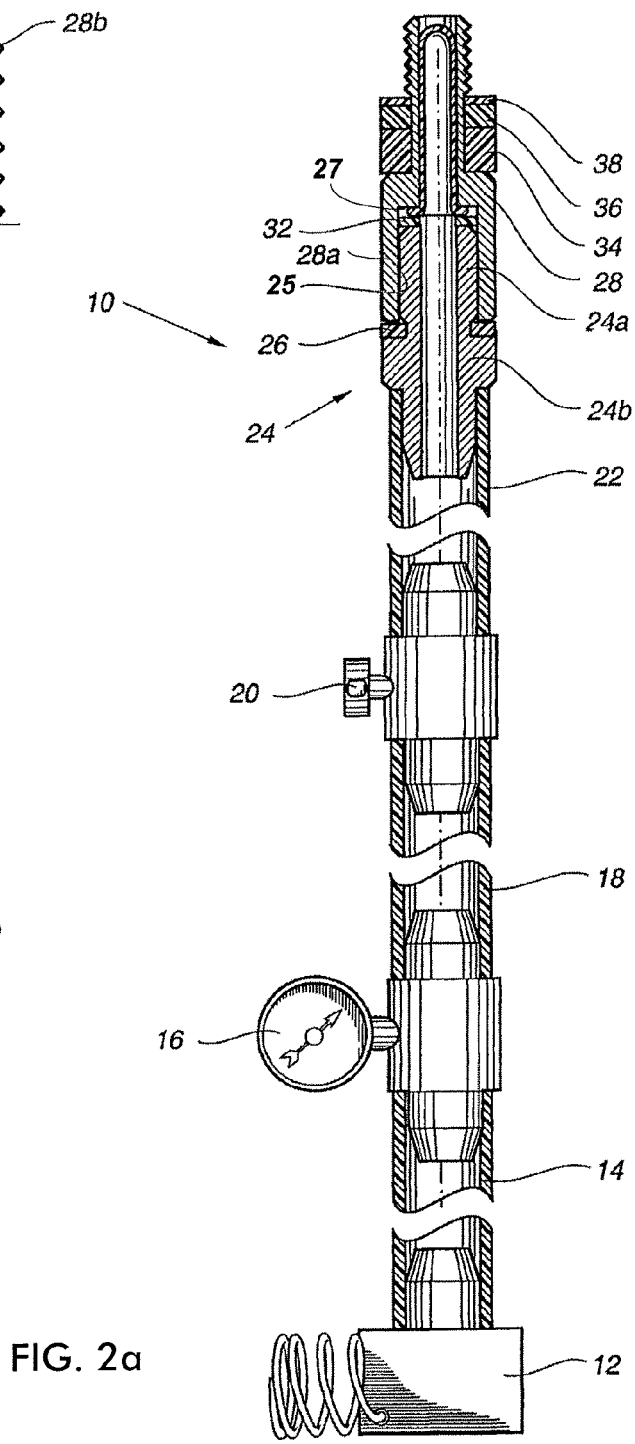
FIG. 2a is a cross-sectional view of the assembly in an assembled position.

In the assembled state (FIG. 2a), the head 30a of the balloon 30 is slightly crimped as seen in FIG. 2b There is further included a seal ring 32 conforming the size of the balloon rim 30c for tightening the rim upon coupling the connector 24 to the probe 28.

Spacer rings 34, 36, 38 or more, of different widths, are included for a reason to be explained below.

For preparation of the sinus membrane lifting there must first be drilled an osteotomy through the alveolar crest where the maxillary dental implant needs to be placed.

Figure 3A:
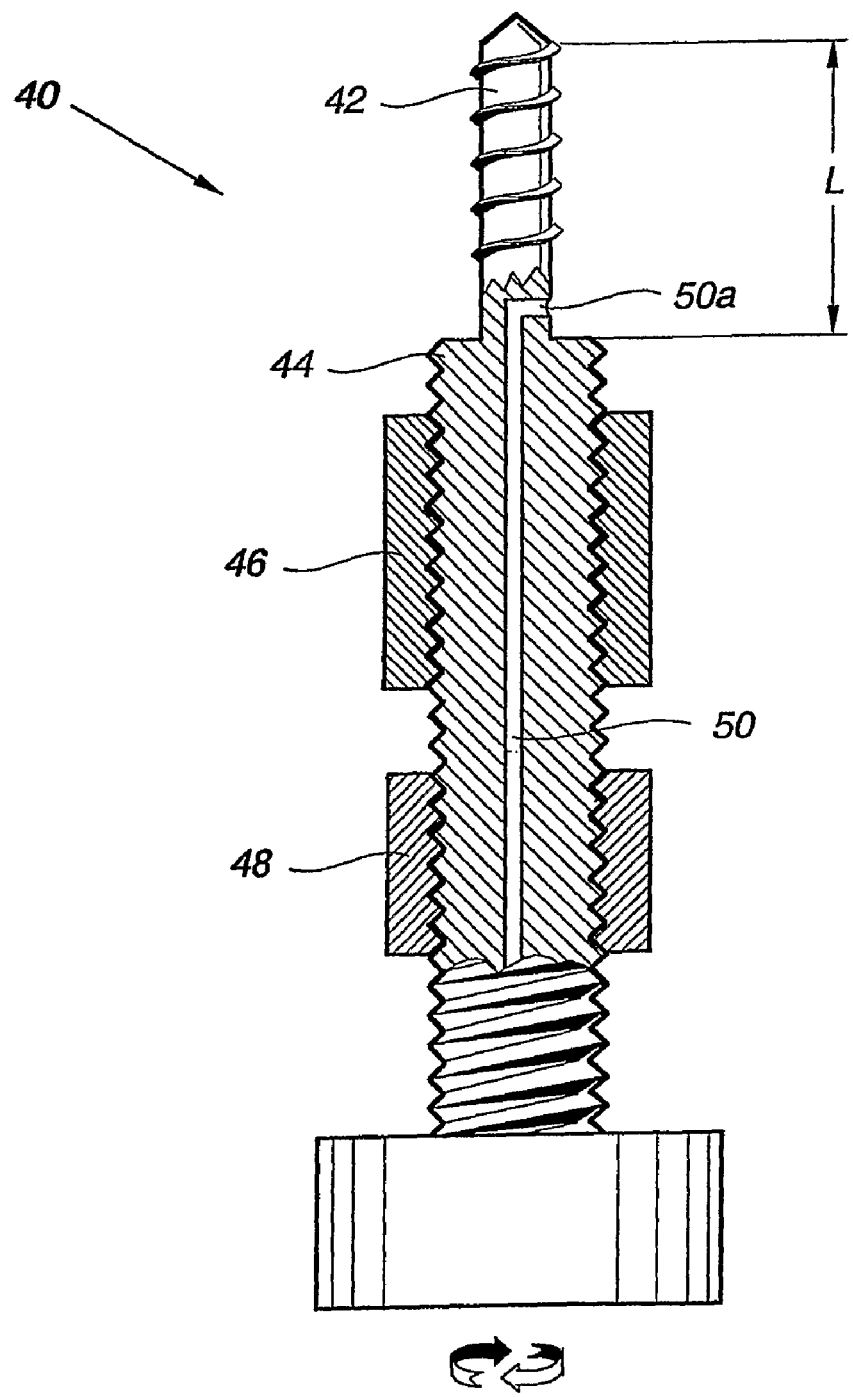
FIGS. 3a and 3b show a drill specially designed for use with the assembly of the present invention.
Figure 3:
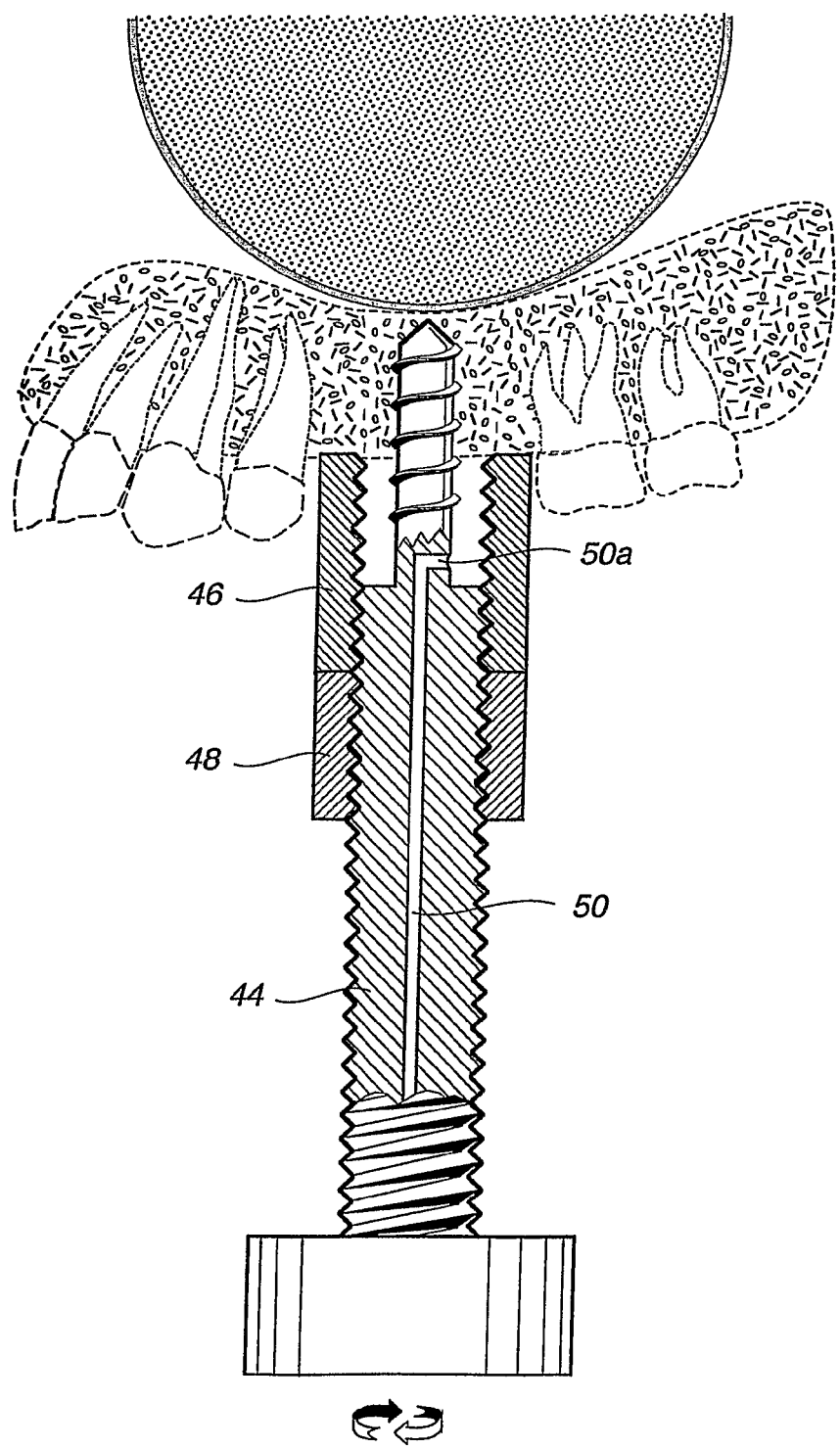

Hence, according to an additional aspect of the present invention a special drilling bit is proposed as shown in FIGS. 3a and 3b.

The osteotomy generally designated 40 comprises a pointed drill 42 of about $2_{mm}$ diameter and a length l of about $8$-$18_{mm}$. Shank 44 is screw-threaded. Set rings 46 and 48 are threadable along the shank 44.

Cooling water flows up the passage 50 and out of outlet 50a.

Depending on the available bone thickness at the alveolar crest (which can vary between $1_{mm}$ to $8_{mm}$), the operative length of the osteotomy drill 42 is preset by the pair of rings 46,48 tightened against each other as shown in FIG. 3b in order that the tip of the drill should reach $1$-$2_{mm}$ below the sinus floor.

Figure 4:
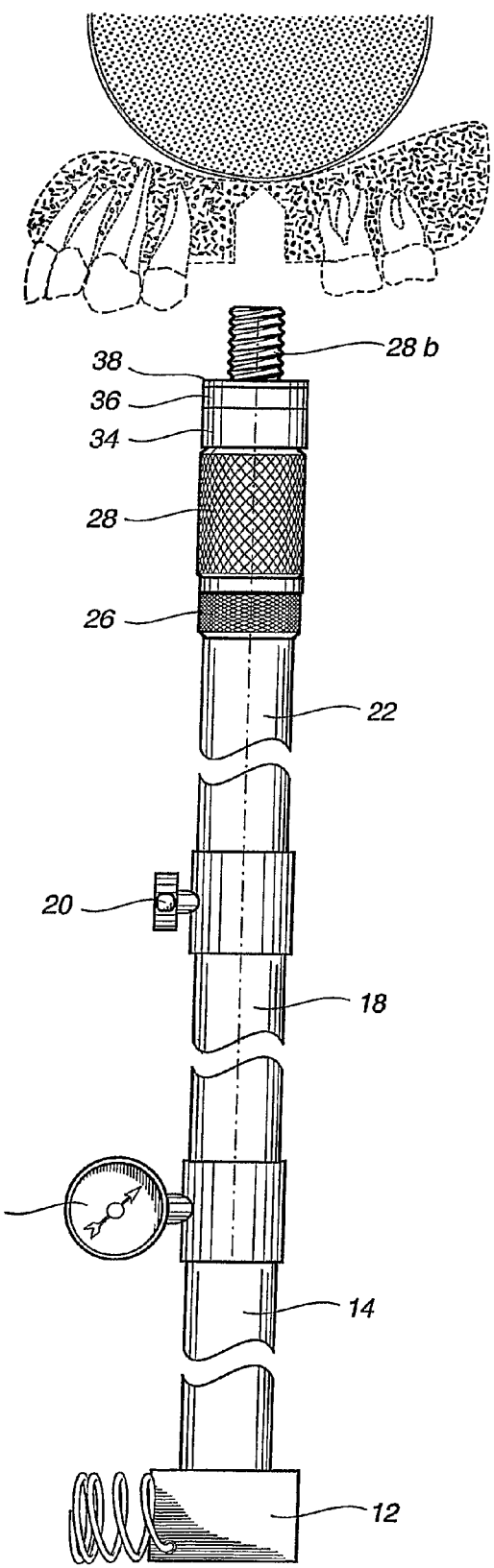
FIG. 4 illustrates the assembly in a preparatory stage.
Figure 5:
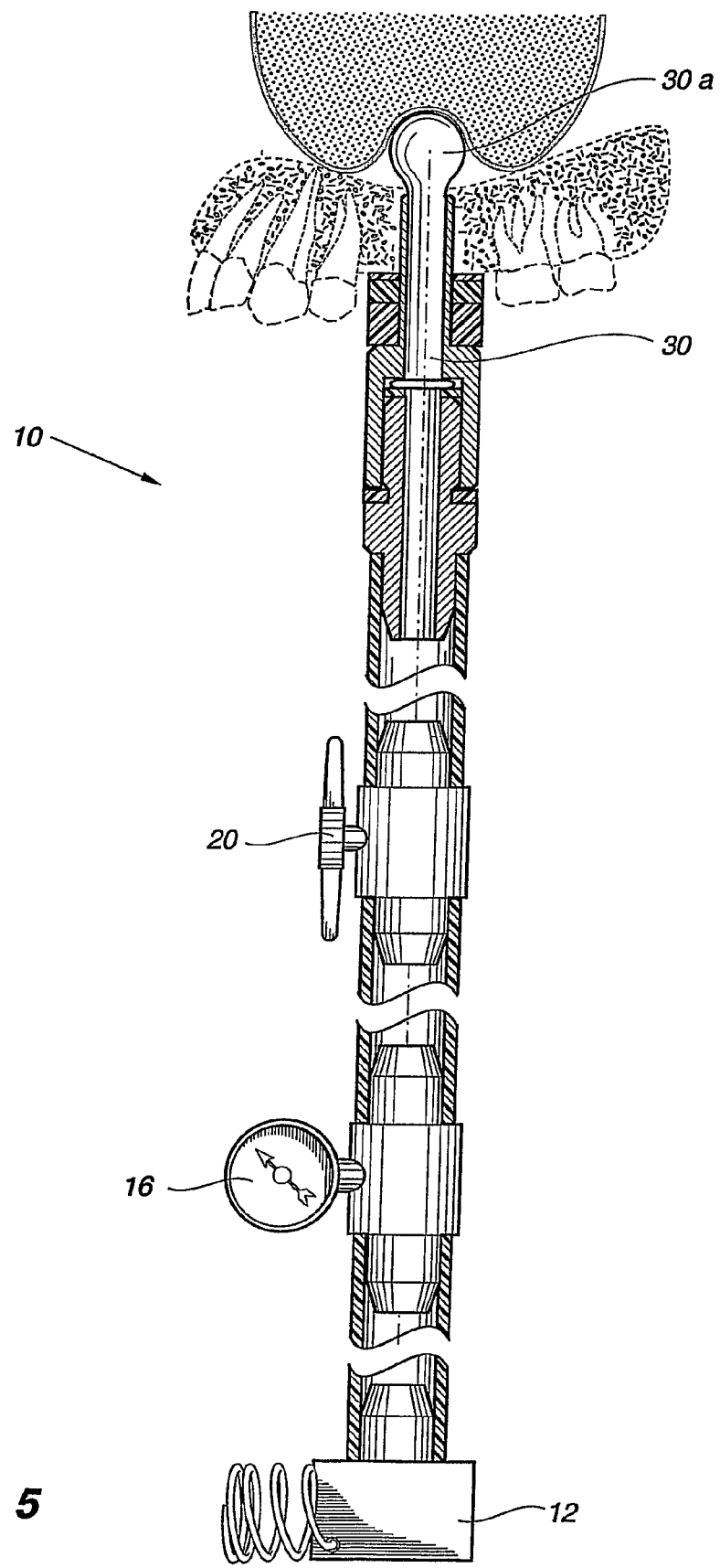
FIG. 5 shows the balloon blowing stage.

The augmentation process proceeds as follows.
(a) The remaining, thin sinus floor above the osteotomy is gently chiseled away by an osteotom (not shown).
(b) The assembly components 20-30 (see FIG. 4) are filled with saline liquid in order to avoid air trapped inside. This is done by simply pouring the liquid into the system (when held upside-down) and then shutting the valve 20.
(c) Spacer rings 34, 36, 38, or any combination thereof are placed over the shoulder 28, around the stem 28b so that after insertion (see below) the top thereof will extend flush with or slightly higher (say by $1_{mm}$) than the sinus floor. This requirement is important in order to avoid rupture of the balloon, once inflated, by sharp bone spikes which remain around the osteotomy after stage (a).
(d) The sub-assembly 20-30 is connected to the pump 12, the valve 20 opened and the pressurized fluid is pumped into the balloon 30—see FIG. 5. Close control should be kept over the process. Typical pressure used is about 2 ata and about $2_{cc}$ in quantity. Monitoring is observed by X-ray or panoramic.
(e) Once the membrane lifting has reached the desired amount, say by balloon inflation of $10_{mm}$-$20_{mm}$ in diameter, the balloon is allowed to deflate (possibly by reversing the pumping direction). It should be emphasized that the blowing of the balloon is carried out in a single, continuous process.
(f) The assembly 10 is removed from the patient, taken apart (see FIG. 1) and sterilized for the next operation.

Figure 6:
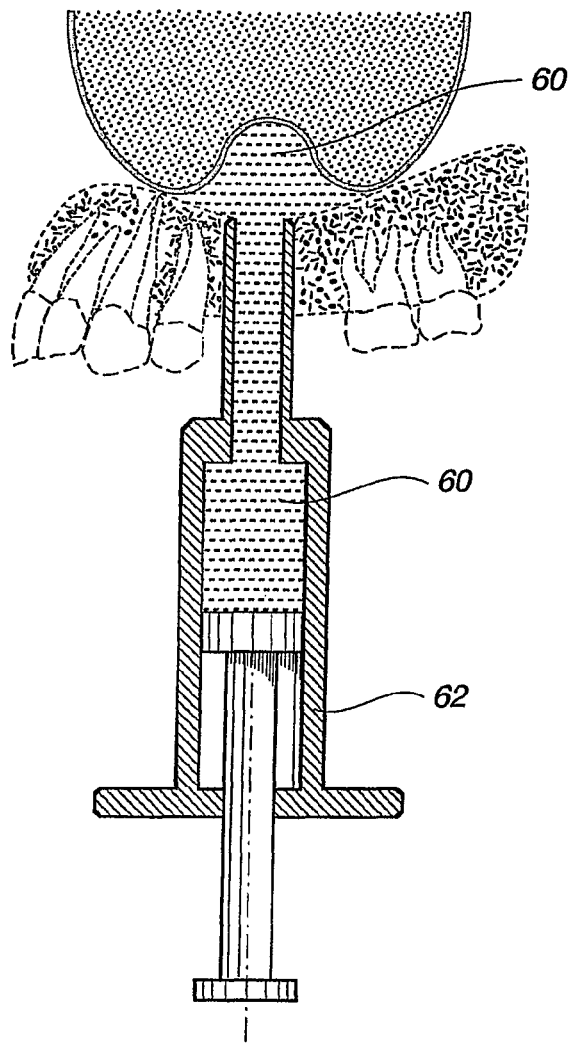
FIG. 6 illustrates the stage of filling the sinus cavity below the elevated membrane with autologous fibrin.

Now the cavity formed under the raised sinus membrane is ready to be filled with fluidized bone substance 60 (artificial or natural), e.g. by using a dedicated syringe 62 as illustrated in FIG. 6.

Figure 7:
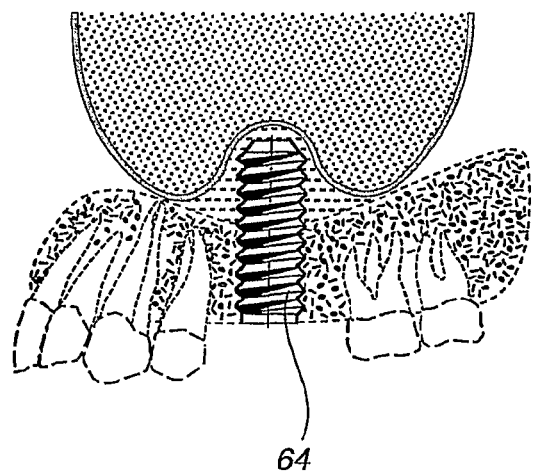
FIG. 7 shows the completed implant placing.

Following the augmentation, implant 64 can be fixed in the conventional manner as shown in FIG. 7. As will be noted, the overall length of the implant can reach $18_{mm}$ and more depending on the individual conditions of each case.

Those skilled in the art to which this invention pertains will readily appreciate that numerous changes, variations and modifications can be effectuated without departing from the true spirit and scope of the invention as defined in and by the appended claims.

What is claimed is:

1. An assembly for performing sinus membrane elevation in a process of dental implant surgery, the assembly comprising:
   a balloon made of an elastomeric material comprising a rounded head portion, an elongated, tubular sleeve portion, and a flanged rim portion;
   a connector member including a screw-threaded portion at one side thereof;
   a balloon probe member including a stem portion with an outer screw-thread and a bore freely fitting the external diameter of the tubular sleeve;
   a cup-shaped portion positioned in said balloon probe member, and including a side wall with an inner screw thread therealong and a base wall comprising a shoulder configured to support said balloon flanged rim portion, when said screw-threaded portion of the connector is threadably received in said cup-shaped portion;
   a flexible pipe comprising a manually operable valve and configured to be coupled to the connector; and
   a pump positioned and configured to administer a pressurized fluid through the pipe to the balloon.

2. The assembly as claimed in claim 1, wherein the rounded head portion of the balloon has a wall thickness less than the wall thickness of the sleeve portion.

3. The assembly as claimed in claim 2, wherein the balloon is made of silicon rubber.

4. The assembly as claimed in claim 3, wherein a modulus of elasticity of the balloon head portion is lower than that of the sleeve portion.

5. The assembly as claimed in claim 4, wherein an elongation factor of the balloon head portion is higher than of the sleeve portion.

6. The assembly as claimed in claim 1, further comprising a pressure-gauge connected to said pipe.

7. The assembly as claimed in claim 6, further comprising a set of discrete spacer rings positioned and configured to limit a penetration depth of the probe in the direction of the sinus floor cavity.

8. The assembly as claimed in claim 1 further including an osteotomy device for drilling a bore at the alveolar crest comprising a drilling bit extended by a screw-threaded shank, a pair of set rings threadably received on the shank adapted, when tightened one against the other, to adjustably limit the depth of the drilled bore.

9. The assembly as claimed in claim 8 wherein the shank is formed with a passage through which cooling water can flow to the vicinity of the bit during the drilling operation.

* * * * *